United States Patent [19]

Cane et al.

[11] 4,059,632
[45] Nov. 22, 1977

[54] PROCESS FOR THE PRODUCTION OF ISOPHORONE

[75] Inventors: Charles Cane; Bertram Yeomans, both of Hull, England

[73] Assignee: BP Chemicals Limited, London, England

[21] Appl. No.: 728,922

[22] Filed: Oct. 4, 1976

[30] Foreign Application Priority Data

Oct. 20, 1975 United Kingdom ............... 42911/75

[51] Int. Cl.² ............................................. C07C 45/00
[52] U.S. Cl. ................................................. 260/586 C
[58] Field of Search .................................... 260/586 C

[56] References Cited

U.S. PATENT DOCUMENTS

| 2,511,630 | 6/1950 | Goren et al. | 260/586 C |
|---|---|---|---|
| 3,337,423 | 8/1967 | Schmitt et al. | 260/586 C |
| 3,337,632 | 8/1967 | Schmitt et al. | 260/586 C |
| 3,337,633 | 8/1967 | Schmitt et al. | 260/586 C |
| 3,462,348 | 8/1960 | Wellman et al. | 260/586 C |
| 3,981,918 | 9/1976 | Walton et al. | 260/586 C |

Primary Examiner—Norman Morganstern
Attorney, Agent, or Firm—Brooks, Haidt, Haffner & Delahunty

[57] ABSTRACT

A process for the production of isophorone involving side-stream removal of a fraction in which color forming compounds are concentrated and treatment thereof with a strong mineral acid to decompose the contaminants into higher boiling compounds. Additionally the bulk of the isophorone is separated from the aqueous phase in the presence of a strong acid which serves to neutralize the alkali catalyst. Such treatment aids phase separation and minimizes beta-isophorone production. Alpha-isophorone is recovered from both fractions.

10 Claims, 1 Drawing Figure

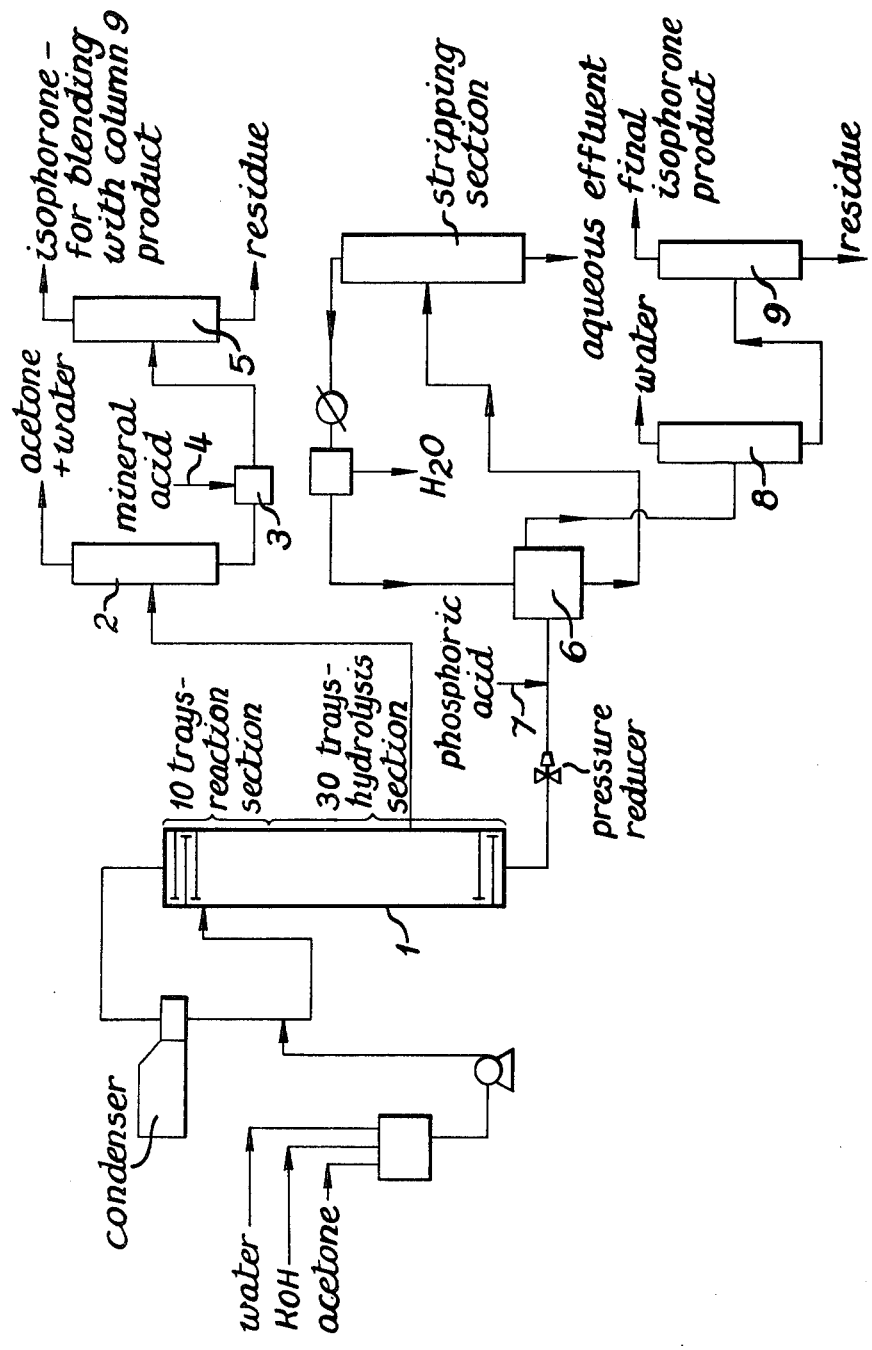

PROCESS FOR THE PRODUCTION OF ISOPHORONE

The present invention provides a process for the production of isophorone by the alkali-catalysed condensation of acetone.

The production of isophorone by the alkali-catalysed condensation of acetone and its separation from the reaction products is a long established process described in German Patent Specifications Nos. 1,144,269; 1,165,018; 1,205,525 and 1,095,818. One method of producing isophorone commercially is to feed acetone and an aqueous solution of an alkali catalyst to the upper section of a pressure distillation reactor which contains a refluxing mixture of acetone/water azeotrope (80:20% w/w respectively) and alkali catalyst (<0.1% w/w) at a temperature in the range 150° to 300° C, usually 200° to 240° C and a pressure in the range 30–35 bar. The lower part of the pressure still operates as a stripping section, from where unconverted acetone passes as an overhead azeotrope product with water and is condensed at the top of the column to produce the reflux. Additionally small amounts of isoxylitone co-produced with the isophorone are hydrolysed back to isophorone and acetone in the lower part of the pressure still. The crude isophorone product leaving the bottom of the pressure still is decanted from the water phase and purified by topping free from water and low-boiling substances and by tailing from the high-boilers in two vacuum stills.

The isophorone produced by this process tends to be contaminated to an undesirable degree with colour-formers which are virtually inseparable from isophorone by simple distillation. Furthermore, the product tends to contain a significant quantity of the beta-isomer of isophorone, the alpha-isomer being the desired product. Whilst it is known to decompose colour-forming contaminants in the bulk product into higher boiling compounds, thereby rendering them more readily separable, by heating with a strong acid, this treatment involves the whole of the product and moreover increases the concentration of the undesirable beta-isomer. Therefore, the treatment of the bulk product with strong mineral acids is undesirable.

It has now been found that because the volatility of the phase containing the colour-formers is intermediate between that of the acetone-water and isophorone-water azeotropes, the colour-formers are concentrated at a point in the column where the acetone content is stripped to a relatively low level. By taking off a side-stream at this point the colour formers can be substantially eliminated from the bulk of the isophorone product and by further treatment pure isophorone can be recovered from the side-stream.

Furthermore addition of strong mineral acid to neutralise the alkali catalyst which is present in the crude isophorone product not only improves the purity of the final product by minimising subsequent production of the beta-isomer content but also aids phase separation from water. The present invention substantially overcomes the disadvantages of the prior art process by providing an integrated process for the production of pure isophorone at high selectivities.

Thus according to the present invention there is provided a process for the production of isophorone which process comprises continuously feeding a mixture comprising acetone, water and an alkali catalyst to an intermediate point in a reaction zone within a column operating at elavated temperature and pressure at such a rate as to maintain an acetone/water azeotrope reflux having an alkali concentration of less than 0.1% w/w within the reaction zone, passing from the bottom of the reaction zone a fraction containing isophorone, water and unconverted acetone to a hydrolysis zone within the same or a different column also operating at elevated temperature and pressure wherein unconverted acetone is separated overhead and returned to the reaction zone, removing at a point in the hydrolysis zone where the acetone concentration is less than 30% w/w a side-stream containing isophorone, acetone, water and colour forming compounds, passing the side-stream to a distillation zone wherein acetone and water are removed in a heading distillation, contacting the base product comprising isophorone and colour-forming compounds from the heading distillation with a strong acid at elevated temperature and recovering isophorone substantially free from colour-forming compounds overhead in a tailing distillation, removing from the base of the hydrolysis zone a bottoms fraction comprising isophorone, water and alkali catalyst, feeding the bottoms fraction together with a sufficient quantity of a strong mineral acid to reduce the pH thereof wherein an isophorone-containing phase is separated and thereafter recovering the isophorone from the isophorone-containing phase.

Whilst the exact chemical nature of the colour-forming compounds is not known they are compounds having boiling points sufficiently close to isophorone to render them difficult to separate from isophorone in a simple distillation column. The present of these compounds in the isophorone leads to discolouration of the final product.

The reaction zone and the hydrolysis zone may be operated as separate columns or, preferably, integrated as separate sections within the same column, the rectification section of the column acting as the reaction zone and the stripping section of the column acting as the hydrolysis zone.

Whilst further alkali may be added to the hydrolysis column it is preferred not to make any such further addition.

The temperature in both the reaction zone and hydrolysis zone may suitably be in the range 150° to 250° C and the pressure may suitably be in the range 10 to 55 bar. The residence time in the reaction zone may be in the range 20 to 120 minutes.

The acetone/water azeotrope reflux in the reaction zone typically has a composition of approximately 80% w/w acetone and 20% w/w water at about 250° C and 32 bar pressure.

Suitable alkali catalysts which may be employed are the alkali metal hydroxides and in particular the hydroxides of sodium and potassium. It is particularly preferred to employ potassium hydroxide as catalyst and operate in the manner described in U.S. Pat. No. 3,981,918 (BP Case No. CH 3740). It is therefore preferred to feed a mixture comprising 65 to 85% w/w acetone, 35 to 15% w/w water and 0.7 to 0.3% w/w potassium hydroxide to an intermediate point in the reaction zone within the column at such a rate as to maintain an acetone/water azeotrope reflux having a potassium hydroxide concentration in the range 300 to 1000 ppm within the reaction zone. It is even more preferable to feed a mixture comprising 65 to 75% w/w acetone, 35 to 25% w/w water and 0.7 to 0.3% w/w potassium hydroxide in order to maintain the acetone/water azeotrope reflux in the reaction zone and the potassium hydroxide concentration in the range 480 to 800 ppm in the reaction zone reflux.

The side-stream is removed from the hydrolysis zone at a point where the acetone concentration is <30% w/w and is preferably <10% w/w.

The bottoms product from the hydrolysis zone may be treated to reduce its pH to a value within the range 5 to 9 with a strong mineral acid selected from phosphoric, sulphuric, hydrochloric and toluene-para-sulphonic acids, of which phosphoric acid is preferred. Preferably the pH is reduced to a value within the range 6.5 to 7.5

Isophorone may be recovered from the isophorone-containing phase separated in the decantation vessel by feeding to a distillation column wherein the last traces of water are removed overhead, removing a bottoms fraction and feeding the bottoms fraction to a further distillation column in which pure isophorone is separated as an overhead fraction.

The distillation zone to which the side-stream from the hydrolysis zone is fed may comprise a single column or a series of columns and may be operated batchwise in the case of a single column or continuously in the case of a series of columns. Since the amount of side-stream product collected amounts to only a small fraction (~3%) of the total isophorone yield it is preferred to operate the distillation zone batchwise by feeding the accumulated side-stream periodically to a distillation column, removing acetone and water overhead, contacting the residue with strong acid at elevated temperature and thereafter recovering isophorone substantially free from colour-forming compounds as an overhead product. It is preferred that the isophorone be taken overhead as quickly as possible to minimise the isomerisation of alpha- to beta-isophorone.

The base product comprising isophorone and colour-forming compounds from the distillation zone may be contacted with a strong mineral acid at a temperature in the range 100 to 240, preferably 140° to 190° C. Suitable strong mineral acids include phosphoric and toluene-para-sulphonic acids of which toluene-para-sulphonic acid is preferred. The strong mineral acid may be added in an amount greater than 0/01% w/w, preferably 0.1 to 5% w/w. The treatment with strong mineral acid at elevated temperature converts the colour-forming compounds to higher-boiling compounds which are more readily separated from isophorone. The duration of the contact and subsequent distillation may be >0.1, preferably from 1 to 50 hours.

Isophorone is useful as a high-boiling solvent for surface coatings, printings inks, polyvinyl chloride processing and as a pesticide. It is a chemical intermediate in the production of a polyamide and a phenol derivative, 3,5-xylenol.

The invention will now be illustrated by the following Examples which are described with reference to the accompanying FIGURE showing a flow-diagram of the plant used.

With reference to the FIG. 1 is a pressure still containing 40 bubble cap plates, the upper 10 plates functioning as a reaction zone and the lower 30 plates functioning as a hydrolysis zone; 2 is a distillation column; 3 is an acid treatment vessel; 4 is a toluene-para-sulphonic acid inlet pipe; 5 is a distillation column; 6 is a decantation vessel; 7 is an aqueous phosphoric acid inlet piep; 8 and 9 are distillation columns.

EXAMPLE 1

Collection of the side-stream concentrate of colour-forming compounds

A mixture comprising 65% w/w acetone, 34.7% w/w water and 0.3% w/w KOH was fed to the 3rd plate from the top of the reaction section of the pressure still 1 at such a rate as to maintain a refluxing azeotropic mixture of acetone an water (ca. 80:20 w/w) at ca. 205° C/32 bar and a potassium hydroxide concentration in the reflux of <0.1% w/w. The acetone was converted to isophorone and by-products including colour-forming compounds which passed down the column in the descending reflux into the hydrolysis section of the column where the unconverted acetone was stripped from the isophorone, the stripped acetone in the form of its water azeotrope passing back up the colum into the reaction section where it finally condensed at the top of column to produce the reflux. A small amount of isoxylitone by-product in the isophorone was hydrolysed back to isophorone an acetone in the hydrolysis section of the column 1. The volatility of the colour-forming compounds in water is intermediate between that of the acetone/water and isophorone/water azeoptropes, resulting in their concentration at a point in he hydrolysis section where the acetone constant is less than 10% w/w.

A side-stream was collected at the 12th plate from the base of the hydrolysis section of the pressure still 1.* This side stream comprised equal amounts by weight of oil and water phase. The oil phase comprised 63% w/w isophorone, 17% w/w mesitylene, 75% w/w of high-boiling substances, 3% w/w acetone and 2% w/w of water.

Production of water-white isophorone from the side-stream product

A sample of the side-stream (1156g, which contained 728.5g of isophorone) was collected from the still 1 as described above and fed to the 20-plate Oldershaw column 2 where acetone and water was removed overhead. 2.6g of toluene-para-sulphonic acid was added to the distillation residue and the mixture was heated to reflux at 140° C/133 m bar for 24 hours. The isophorone fraction (721g, equivalent to 99% recovery) was then taken overhead at a reflux ratio of 1:1. The isophorone distillate product contained 8.9% w/w of beta-isophorone, and gave a colour test result of 0.6 Lovibond yellow units in a 15 cm cell.*

Neutralisaton of crude isophorone to give final product of low beta-isomer content The emulsified base product from the hydrolysis section of the still 1, which comprises one volume of crude isophorone per 5 volumes of water and 0.13% w/w of potassium hydroxide was mixed with aqueous 10% w/w phosphoric acid (5.5 cm³/h) fed through line 7. This mixture (pH 7 units) was then fed (feed rate 460 cm³/h) into the decantation vessel 6 (volume 250 cm³). The isophorone-containing phase removed contained 2.1 ppm of potassium ion (determined spectrophotometrically), 90% w/w of alpha-isophorone and 0.12% w/w of beta-isophorone. The decanted oil phase was fed to distillation column 8 where water was removed overhead and the base product was fed to distillation column 9 operating at 130 m bar and isophorone recovered as a distillate fraction. The isophorone distilled off contained 0.9% w/w of beta-isophorone and gave a colour test result of 0.8 Lovibond yellow units/15 cm cell.* A blend of this isophorone product and isophorone recovered from the side-stream contained 1.1 % w/w of beta isophorone and gave a colour test result of 0.8 Lovibond yellow units/15 cm cell.* Thus the overall selectivity to isophorone was increased without failure to meet an acceptable specification colour and Engler boiling range tests.

COMPARISON TEST A

Example 1 was repeated except that the side-stream was not treated with strong mineral acid. The recovered isophorone fraction gave a colour test result of 130 Lovibond units of yellow/15 cm cell.* The main isophorone distillate product gave a test result of 0.7 units of yellow. This test shows that the colour-forming compounds were concentrated in the side-stream. The amount of side-stream product collected corresponded at 3% of the isophorone yield.

*Purity Tests — The basic features of colour and boilin range tests for petrochemicals are laid down in B.S.S. 950 (1967) and B.S.S. 658 (1962)/4591 (1971) respectively.

EXAMPLES 2 to 7

Example 1 was repeated with different amounts of toluene-para-sulphonic acid and different mineral acids added to the side-stream product from whih acetone and water had been removed and also with different periods of treatment. The conditions used and the results obtained are given in Table 1.

EXAMPLES 8 to 10

Example 1 was repeated with varying additions of phosphoric acid under the conditions and with the results shown in Table 2.

The results given in Table 2 show that the alkali metal ion content of the crude isophorone stream from the botton of the hydrolysis zone is reduced from 40 to 2–3 ppm by neutralisation of the emulsion. It might be expected that the consequent decrease in the deposition of inorganic salts in the distillation columns 8 and 9 would lead to an increase in the operating time between main plant shutdowns for cleaning. The reduction in the beta-isophorone content allows isophorone of higher beta-content recovered from the side-stream to be blended in to the main product whilst maintaining an acceptable overall specification for the combined product.

Comparison Test B is not an example according to the invention.

TABLE 2

| Ex. No. | Decanted Isophorone Phase | | Main Isophorone Distillate Product" | |
|---|---|---|---|---|
| | pH | K+ (ppm) | Beta-isophorone (% w/w) | Colour (Lovibond Yellow Units) |
| 8 | 5.8 | 3.0 | 0.66 | 0.8 |
| 9 | 7.1 | 2.1 | 0.9 | 0.8 |
| 10 | 9.0 | 2.5 | 1.5 | 0.7 |
| Comparison Test B | 12.2' | 40 | 2.3 | 1.0 |

'phosphoric acid addition was not made
"acceptable specification limits
 (i) ≯2.5% w/w of beta-isophorone
 (ii) ≯1 unit of yellow/15 cm. cell*

We claim:

1. A process for the production of isophorone which process consists of continuously feeding a mixture consisting of acetone, water and an alkali catalyst to an intermediate point in a reaction zone within a column operating at elevated temperature and pressure at such a rate as to maintain an acetone/water azeotrope reflux having an alkali concentration of less than 0.1% w/w within said reaction zone, passing from the bottom of said reaction zone a fraction containing isophorone, water and unconverted acetone to a hydrolysis zone within said column or a second column also operating at elevated temperature and pressure wherein unconverted acetone is separated overhead and returned to said reaction zone, removing at a point in said hydrolysis zone where it acetone concentration is less than 30% w/w a side-stream containing isophorone, acetone, water and colour-forming compounds, passing said side-stream to a distillation zone wherein actor and water are removed in a heading distillation, contacting the base product consisting of isophorone and colour-forming compounds from said heading distillation with a strong acid at elevated temperature and recovering isophorone substantially free from colour-forming compounds overhead in a tailing distillation, removing from the base of said hydrolysis zone a bottoms fraction consisting of isophorone, water and said alkali catalyst, feeding said bottoms fraction together with a sufficient quantity of a strong mineral acid to reduce the pH thereof to a value within the range 5 to 9 to a decantation vessel wherein an isophorone-containing phase is separated and thereafter recovering said isophorone from said isophorone-containing phase.

2. A process according to claim 1 wherein said reaction zone and said hydrolysis zone are integrated as separate sections within the same column, the rectification section of said column acting as said reaction zone and the stripping section of said column acting as said hydrolysis zone.

TABLE 1

| Ex. No. | Addition (% w/w) | Heat Treatment Duration (h) | Heat Treatment Temp °C | Colour of Recovered Isophorone*** Without Treatment | Colour of Recovered Isophorone*** After Treatment | Beta-isophorone Content of recovered isophorone (% w/w) |
|---|---|---|---|---|---|---|
| 2 | 0.05, TpSA* | 7.5 | 190 | 130 | 4.0 | 6.7 |
| 3 | 0.1, TpSA* | 7 | 190 | 130 | 1.3 | 9.3 |
| 4 | 0.1, TpSA* | 11 | 190 | 130 | 0.6 | 4.9 |
| 5 | 0.5, TpSA* | 24 | 140 | 130 | 0.6 | 8.9 |
| 6 | 2.0, TpSA* | 0** | 130 | 130 | 0.6 | 9.2 |
| 7 | 0.5, H$_3$PO$_4$ | 24 | 140 | 130 | 1.7 | 18.0 |

*TpSA is an abbreviation for toluene-para-sulphonic acid
**The isophorone was taken overhead without prior heat treatment
***Lovibond units of yellow in a 15 cm. cell 3. A process according to claim 1 wherein said elevated temperature is in the range 150° to 250° C and said elevated pressure is in the range 10 to 55 bar.

4. A process according to claim 1 wherein said alkali catalyst is a hydroxide of an alkali metal selected from sodium and potassium.

5. A process according to claim 1 wherein said mixture fed at said intermediate point in said reaction zone consists of from 65 to 85% w/w acetone, 35 to 15% w/w water and from 0.7 to 0.3% w/w potassium hydroxide and is fed at such a rate as to maintain an acetone/water azeotrope reflux having a potassium hydroxide concentration in the range from 300 to 1000 ppm within the reaction zone.

6. A process according to claim 1 wherein said strong mineral acid contacted with said bottoms fraction from said hydrolysis zone is selected from phosphoric acid, sulphuric acid, hydrochloric acid and toluene-para-sulphonic acid.

7. A process according to claim 1 wherein said isophorone is recovered from said isophorone-containing phase separated in said decantation vessel by feeding said phase to a distillation column wherein the last traces of water are removed overhead, removing a bottoms fraction and feeding said bottoms fraction to a further distillation column in which pure isophorone is separated as an overhead fraction.

8. A process according to claim 1 wherein said distillation zone to which said side-stream from said hydrolysis zone is fed is operated batchwise by feeding the accumulated side-stream periodically to a distillation column, removing acetone and water overhead, contacting the residue with strong acid in an amount greater than 0.01% w/w at a temperature in the range 100 to 240° C and thereafter recovering isophorone substantially free from colour-forming compounds as an overhead product.

9. A process according to claim 8 wherein said strong mineral acid is selected from phosphoric acid and toluene-para-sulphonic acid in an amount in the range from 0.1 to 5% w/w.

10. A process according to claim 1 wherein said side-stream is removed at a point in said hydrolysis zone wherein the acetone concentration is less than 10% w/w.

* * * * *

UNITED STATES PATENT AND TRADEMARK OFFICE
CERTIFICATE OF CORRECTION

PATENT NO. : 4,059,632

DATED : November 22, 1977

INVENTOR(S) : CHARLES CANE and BERTRAM YEOMANS

It is certified that error appears in the above-identified patent and that said Letters Patent are hereby corrected as shown below:

Col. 2, line 33, "present" should read --presence--

Col. 3, line 67, "piep" should read --pipe--.

Col. 4, line 6, after "fed" and before "to" insert --on-- line 9, after "acetone" and before "water" "an" should read --and--.

line 26, "he" should read --the-- line 33, "75% w/w" should read --7% w/w-- line 39, after "the" and before "still" insert --pressure-- line 55, "comprises" should read --comprised--

Col. 5, line 20, "at" should read --to-- line 21, "boilin" should read --boiling-- line 27, "whih" should read --which--

(cont'd.)

UNITED STATES PATENT AND TRADEMARK OFFICE
CERTIFICATE OF CORRECTION

PATENT NO. : 4,059,632
DATED : November 22, 1977
INVENTOR(S) : CHARLES CANE and BERTRAM YEOMANS It is certified that error appears in the above-identified patent and that said Letters Patent are hereby corrected as shown below:

Table 1, 2nd column headed "Addition", insert --Catalyst-- before "Addition"

Claim 1, line 30, "it" should read --the-- line 33, "actor" should read --acetone--

Signed and Sealed this

Thirtieth Day of May 1978

[SEAL]

Attest:

RUTH C. MASON
Attesting Officer

LUTRELLE F. PARKER
Acting Commissioner of Patents and Trademarks